US00PP21082P2

(12) United States Plant Patent
Krassenburg

(10) Patent No.: US PP21,082 P2
(45) Date of Patent: Jun. 22, 2010

(54) ***IMPATIENS* PLANT NAMED 'SILT CHER'**

(50) Latin Name: *Impatiens walleriana*
Varietal Denomination: Silt Cher

(75) Inventor: Jolanda Krassenburg, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 80 days.

(21) Appl. No.: 12/313,322

(22) Filed: Nov. 19, 2008

(51) Int. Cl.
*A01H 5/00* (2006.01)

(52) U.S. Cl. ..... Plt./317

(58) Field of Classification Search ..... Plt./317
See application file for complete search history.

(56) References Cited

U.S. PATENT DOCUMENTS

| | | | | |
|---|---|---|---|---|
| PP15,865 | P2 * | 7/2005 | Heffner | Plt./317 |
| PP15,905 | P2 * | 8/2005 | Jonkers | Plt./317 |
| PP18,007 | P2 * | 9/2007 | Jonkers et al. | Plt./317 |
| 2006/0041973 | P1 * | 2/2006 | Cascante | Plt./317 |

OTHER PUBLICATIONS

UPOV ROM GTITM Computer Database, GTI Jouve Retrieval Software 2009/05 Citation for 'Silt Cher'.*

* cited by examiner

*Primary Examiner*—Wendy C. Haas
(74) *Attorney, Agent, or Firm*—S Matthew Edwards

(57) ABSTRACT

A new *Impatiens* plant named 'Silt Cher,' particularly distinguished by rose-shaped, double type flowers, light cherry red to carmine flower color, dark green foliage, relatively round leaf shape, medium vigor, and well-branched, low and mounding habit.

1 Drawing Sheet

Latin name of the genus and species of the plant claimed: *Impatiens walleriana.*

Varietal denomination: 'Silt Cher'.

BACKGROUND OF THE NEW PLANT

The present invention comprises a new *Impatiens*, botanically known as *Impatiens walleriana,* and hereinafter referred to by the variety name 'Silt Cher.'

'Silt Cher' is a product of a planned breeding program. The new cultivar 'Silt Cher' has light cherry red to carmine flower color, rose-shaped, double type flowers, dark green foliage, and low and mounding plant habit.

'Silt Cher' originated from a hybridization made in April 2003 in a controlled breeding program in Andijk, Netherlands. The female parent was an unpatented hybrid seedling identified as 'ID03-25-2' with salmon flower color and single flower type.

The male parent of 'Silt Cher' was an unpatented hybrid seedling identified as 'ID03-29-2' with carmine colored, single-type flowers.

The resulting seeds were sown in June 2003. 'Silt Cher' was selected as one flowering plant within the progeny of the stated cross in August 2003 in a controlled environment in Andijk, Netherlands.

The first act of asexual reproduction of 'Silt Cher' was accomplished when vegetative cuttings were taken from the initial selection in the fall of 2004 in a controlled environment in Andijk, Netherlands.

Horticultural examination of plants grown from cuttings of the plant initiated in the spring of 2004 in Andijk, Netherlands, and continuing thereafter, has demonstrated that the combination of characteristics as herein disclosed for 'Silt Cher' are firmly fixed and are retained through successive generations of asexual reproduction.

'Silt Cher' has not been observed under all possible environmental conditions. The phenotype may vary significantly with variations in environment such as temperature, light intensity and day length.

Plant Breeder's Rights for this cultivar were applied for in Canada on Dec. 24, 2007 and in the European Union on Jul. 21, 2008. 'Silt Cher' has not been made publicly available more than one year prior to the filing of this application.

DESCRIPTION OF THE DRAWINGS

The accompanying photographic drawing shows typical flower and foliage characteristics of 'Silt Cher' with colors being as true as possible with an illustration of this type. The photographic drawing, taken in late May 2008, shows a 15 week old greenhouse grown plant of the new variety.

DETAILED BOTANICAL DESCRIPTION

The measurements were taken in Hillscheid, Germany, mainly in late May 2008 on 14-15 week old plants that were growing on benches in a greenhouse. Culture of these plants had started around February 10 when rooted cuttings were potted in 12 cm pots and grown at moderately warm temperatures, between 15 and 20° C. in daytime.

Color Chart used: Royal Horticultural Society Colour Chart (RHS) 2001.

BRIEF SUMMARY OF INVENTION

The following observations, measurements, and comparisons describe plants grown in a greenhouse in Hillscheid, Germany. The following traits have been repeatedly observed and are determined to be basic characteristics of the new variety. The combination of these characteristics distinguishes this *Impatiens* as a new and distinct variety.

1. Light cherry red to carmine, double-type flowers
2. Dark green foliage, relatively round leaf shape
3. Well branched and relatively low and mounding plant habit
4. Medium plant size
5. Suitable as a bedding plant, for containers and as a flowering pot plant near or in the house.

COMPARISON WITH COMMERCIAL CULTIVARS

'Silt Cher' differs from the commercial variety 'Didi Chered,' U.S. Plant Pat. No. 15,905, in that 'Silt Cher' has somewhat smaller flowers, stronger branching and a more compact plant habit.

'Silt Cher' differs from the commercial variety 'Silte Rossa,' U.S. Plant Pat. No. 18,007, by having a somewhat more reddish overall flower color and by a more vigorous growth habit.

Plant:

*Form, growth and habit.*—Semi-spherical, somewhat flattened.

*Plant height.*—9-11 cm.

*Plant height* (*inflorescence included*).—11-14 cm.

*Plant width.*—28-32 cm.

*Plant size in late summer* (30 *weeks old*).—25-28 cm in height, 37-42 cm in diameter.

Stem:

*Number of branches.*—12-15.

*Color of stem.*—Pale green, RHS 146D, with purple color, RHS 185C to 185D, near the nodes and as fine speckles.

*Length of stem.*—About 10-15 cm.

*Diameter.*—0.5-0.8 cm at the middle part.

*Length of internodes.*—Approximately 2-4 cm.

*Texture.*—Smooth, glabrous.

Foliage:

*Arrangement.*—Mainly alternate, simple.

*Immature, leaf color, upper surface.*—RHS 139A, dark green.

*Lower surface.*—RHS 146B and splotches of RHS 185C.

*Mature, leaf color, upper surface.*—Near RHS 147A, or between RHS 137A and RHS 147A, dull.

*Lower surface.*—RHS 146B and splotches of RHS 185C, dull purple.

*Length.*—5.5-7.5 cm.

*Width.*—3.5-4.5 cm.

*Shape.*—Ovate to nearly round or rhomboid, pinnate venation.

*Base shape.*—Attenuate/acute.

*Apex shape.*—Acuminate to cuspidate.

*Margin.*—Slightly crenate, ciliate.

*Texture.*—Both surfaces nearly glabrous, a few short hairs.

*Color of veins, upper surface.*—RHS 147B.

*Color of veins, lower surface.*—RHS 146B.

Petiole:

*Color upper surface.*—RHS 145D, may be weakly infused with RHS 51D.

*Color lower surface.*—RHS 145C to 158D.

*Length.*—2.5-4.5 cm.

*Diameter.*—0.3 cm.

*Texture.*—Mainly glabrous.

Inflorescence:

*Duration of flowering.*—Continuous flowering from spring through fall, indoors longer, depending on light intensity and temperature.

*Start of flowering.*—6-7 weeks after planting of rooted cuttings.

*Inflorescence type.*—Emerge from the upper leaf nodes, peduncles bear one or two flowers.

*Number of flowers and buds per branch.*—More than 10, in various stages of development Peduncle:

*Color.*—RHS 145B, pale green.

*Length.*—Most often 2.5-3.0 cm.

*Diameter.*—0.2-0.3 cm.

*Texture.*—Flexible, glabrous.

Pedicel:

*Color of pedicel.*—Light green.

*Length of pedicel.*—Approximately 2.0-2.5 cm.

*Diameter of pedicel.*—0.15-0.2 cm.

*Texture.*—Smooth, glabrous.

Flower:

*Form.*—Double-type, many-petalled.

*Shape of corolla.*—Round outline, rose-shape.

*Number of petals.*—More than 20.

*Overall color.*—Cherry red, appears more reddish than RHS N57B, but a little deeper than RHS 52A.

*Upper surface color, close.*—Near RHS N57B, slightly more reddish; banner petal with a middle stripe of red, RHS 45B.

*Markings.*—No real markings.

*Lower surface color.*—RHS 50B to RHS 52B.

*Diameter of flower.*—4.0-4.5 cm.

*Depth of flower.*—1.9-2.1 cm.

*Fragrance.*—None.

*Longevity.*—Flowers last 5-8 days in greenhouse.

*Rain tolerance.*—Fair, but placing it under light rain protection may improve flower quality.

Petals:

*Shape.*—Banner petal cordate, lateral and lower petals ovate or obovate.

*Apex shape.*—Rounded or emarginate.

*Base.*—Attenuate.

*Margin.*—Entire.

*Size of outer petals size, top* (*'banner'*) *petal.*—Length: 1.9-2.0 cm. Width: 2.8-3.0 cm.

*Size, lateral and lower petals.*—Length: 2.3-2.5 cm. Width: 1.9 -2.1 cm.

*Size of inner petals.*—Diminishing in size.

*Petal texture.*—Smooth, glabrous.

BUD (just before opening):

*Shape.*—Ovoid.

*Length.*—2.1 cm.

*Diameter.*—1.7 cm.

*Color.*—Near RHS 50B.

Calyx:

*Number of sepals.*—5, one of which is transformed into a spur.

*Sepal shape.*—Largest one fused with banner petal, lateral sepals small, lanceolate, and lower sepals are fused, ovate and bearing the spur.

*Apex shape.*—Acute to acuminate.

*Base shape.*—Rounded.

*Margins.*—Entire.

*Color of lateral sepals.*—Brown, near RHS 174A.

*Color of lower sepals.*—Light brown, semi-transparent, RHS 174B.
*Length of lateral sepals.*—0.5 cm.
*Width of lateral sepals.*—0.2 cm.
*Length of lower sepals.*—1.3 cm.
*Width of lower sepals.*—0.9 cm.
*Texture.*—Glabrous.

Spur:
*Aspect of spur.*—Slanting downwards.
*Length of spur.*—3.9-4.3 cm.
*Diameter of spur.*—0.2 cm.
*Color of spur.*—RHS 146D to mainly close to 174D.

Reproductive organs: Usually none, only occasionally in rudimental form, as all stamen are transformed into petals.
*Fertility/seed set.*—Infertile, no seed set observed.

Disease/pest resistance: Disease resistance or susceptibility has not been observed on this hybrid.

What is claimed is:

1. A new and distinct variety of *Impatiens* plant named 'Silt Cher,' substantially as illustrated and described herein.

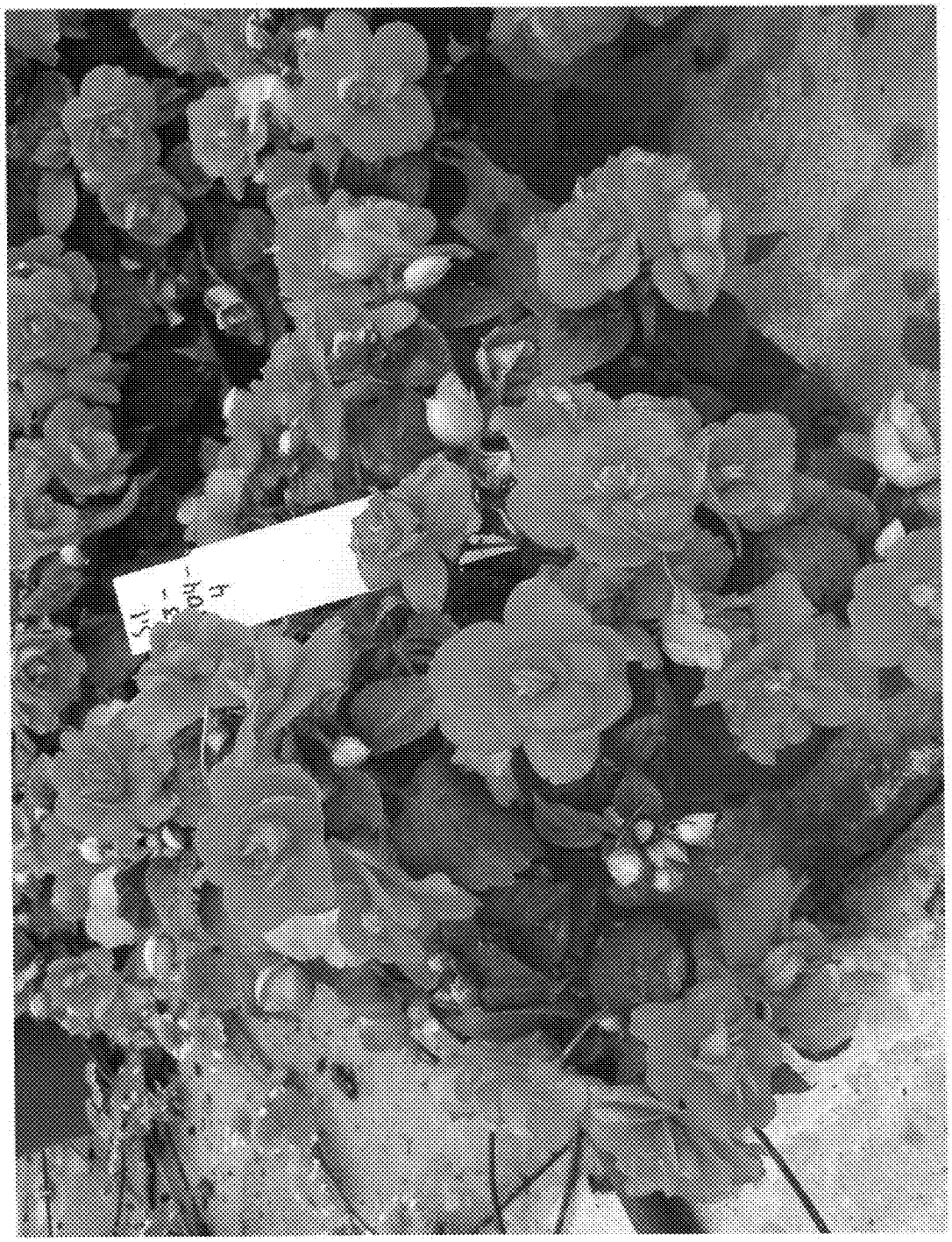

* * * * *